(12) United States Patent
Bar Shalev

(10) Patent No.: US 7,024,028 B1
(45) Date of Patent: Apr. 4, 2006

(54) METHOD OF USING FRAME OF PIXELS TO LOCATE ROI IN MEDICAL IMAGING

(75) Inventor: Avi Bar Shalev, Kiryat-Haim (IL)

(73) Assignee: Elgems Ltd., Haifa ( * ) Notice: Subject to any disclaimer, the term of this patent is extended or adjusted under 35 U.S.C. 154(b) by 0 days.

(21) Appl. No.: 09/572,218

(22) Filed: May 17, 2000

(30) Foreign Application Priority Data

Oct. 7, 1999 (IL) .................................... 132266

(51) Int. Cl.
G06K 9/00 (2006.01)

(52) U.S. Cl. ........................................ 382/131; 345/422

(58) Field of Classification Search ................ 382/128, 382/130–132, 174, 190
See application file for complete search history.

(56) References Cited

U.S. PATENT DOCUMENTS

| | | | |
|---|---|---|---|
| 5,523,571 A | * | 6/1996 | Velazquez et al. ..... 250/363.05 |
| 5,554,848 A | | 9/1996 | Hermony et al. |
| 5,570,404 A | | 10/1996 | Liang et al. |
| 5,899,863 A | * | 5/1999 | Hatfield et al. .............. 600/443 |
| 5,961,457 A | * | 10/1999 | Raylman et al. ............. 600/436 |
| 5,995,108 A | * | 11/1999 | Isobe et al. .................. 345/421 |
| 6,058,218 A | * | 5/2000 | Cline .......................... 382/254 |
| 6,102,861 A | * | 8/2000 | Avila et al. .................. 600/443 |
| 6,122,541 A | * | 9/2000 | Cosman et al. ............. 600/426 |
| 6,177,675 B1 | * | 1/2001 | Gagnon et al. .......... 250/363.1 |
| 6,674,894 B1 | * | 1/2004 | Parker et al. ................ 382/154 |

FOREIGN PATENT DOCUMENTS

WO    WO 98/24058    * 6/1998

OTHER PUBLICATIONS

"Enhanced Image Detail Using Continuity in the MIP Z-Buffer: Applications to Magnetic Resonance Angiography" by Parker et al. Journal of Magnetic Resonance Imaging vol. 11, pp. 378-388, Apr. 2000.*

* cited by examiner

*Primary Examiner*—Samir Ahmed
*Assistant Examiner*—Charles Kim
(74) *Attorney, Agent, or Firm*—Fenster & Company

(57) ABSTRACT

A method of using a frame of pixels of a specified characteristic such as a maximal intensity projected frame and a depth location "virtual" frame to locate and image ROI's in patients.

22 Claims, 4 Drawing Sheets

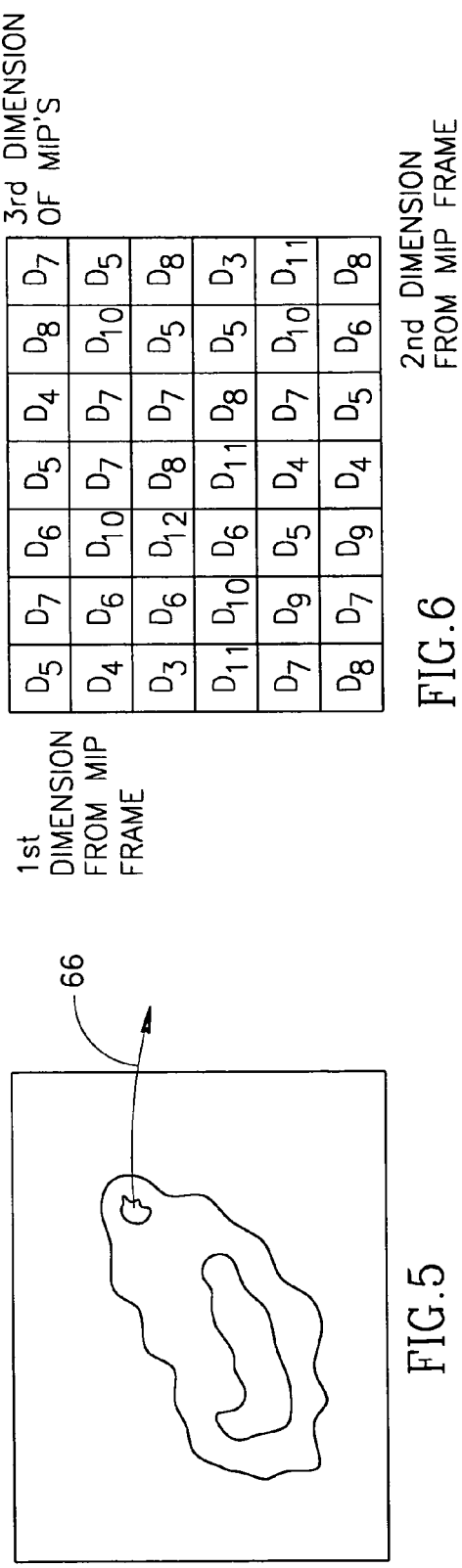
FIG.5
FIG.6
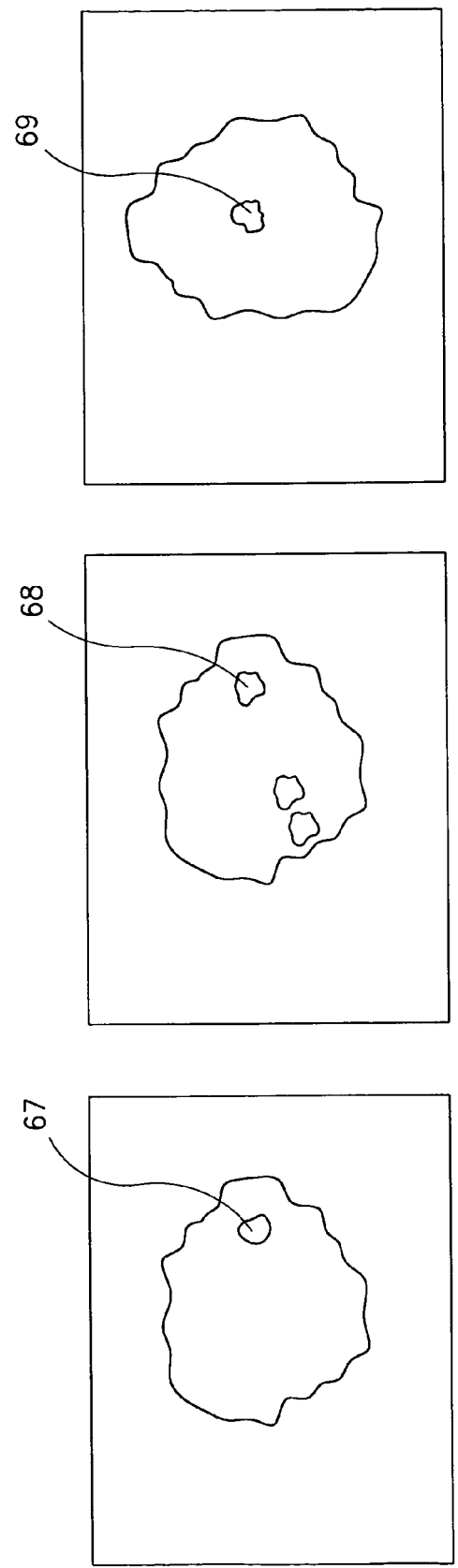
FIG.7A
FIG.7B
FIG.7C

METHOD OF USING FRAME OF PIXELS TO LOCATE ROI IN MEDICAL IMAGING

FIELD OF THE INVENTION

This invention relates generally to single proton emission computerized tomography (SPECT) and more particularly to apparatus and methods for locating and displaying various regions of interest (ROI) within the patient being subjected to computerized tomographic imaging.

BACKGROUND OF THE INVENTION

SPECT imaging produces two-dimensional tomograms; that is, planar images of the body that are generally oriented either in an axial direction, coronal direction or a sagittal direction. In applying imaging methods, it is well-known to acquire images of multiple slices in the body. This is done either by helical scanning or by individual circular scans while moving the patient step-by-step relative to the scanner.

At the present time, in order to locate a particular ROI in three dimensions in the body, such as one containing a lesion, it is necessary for the radiologist or physician to inspect the many parallel images that have been acquired. For example in a whole body scan it is not unusual to acquire as many as 200 parallel images having one or more of axial, coronal or sagittal orientations. The physician or radiologist in charge of the examination then studies each of the 200 images to determine the location of the lesion in the body. When the location of the lesion is determined, then more detailed scans are undertaken to provide maximum information about the lesion. For example, if the lesion is discovered in an image in the axial plane, then the operator of the equipment will acquire sagittal and coronal, as well as more axial images in the region of interest, to further examine the lesion, for surgical planning, for example. To discover specific lesions, the physician or radiologist in charge of examination must look for "hot" spots that are on the order of one square centimeter, a very time-consuming job.

At the present time, some of the ways used to lessen the burden of reviewing the large group or set of images of slices include cinematic displays of the slice set, and/or a cinematic display of a volume rendered as a 3-D presentation. When using the first of these prior art solutions, the user has to concentrate on the moving presentation in which only one slice is activated at a time. When a lesion is detected, the viewer has to immediately stop the cinematic display and use a cursor to point to the lesion. Then, additional images are taken at the point that the cursor is positioned.

When cinematic volumetric images are displayed, according to the second prior art solution, the display gathers into one view the 3-D information of the slices. Here again, when the lesion is found the viewer has to immediately pause the movie and point to the lesion with the cursor. Then, additional views are taken at the cursor location. These prior art solutions often require additional viewing to locate a lesion.

Maximum intensity projection (MIP) are known in the prior art. It is a commonly used technique in imaging for such things as for displaying 3-D vascular image data. For example, see U.S. Pat. No. 5,570,404 the disclosure of which is hereby included herein by reference. In that patent, the MIP is used for removing undesirable structures from a series of parallel images. As noted in the patent, the MIP frame is developed from a stack of acquired parallel images. The MIP frame contains pixels, wherein each pixel holds the maximum intensity along a ray perpendicular to the MIP frame. The patent does not use the MIP for locational purposes. A preferred aspect of the present invention is to use MIP's for locating regions of interest in a patient being imaged, for example, for locating lesions in the patient. A preferred aspect of the invention also includes displaying the located lesions in three orthogonal planes, or in a 3-D image.

SUMMARY OF THE INVENTION

Thus, a preferred aspect of some preferred embodiments of the invention relates to a method for expeditiously locating and displaying particular regions of interest in a patient or object being imaged. The method includes:

acquiring a plurality of parallel frames of two-dimensional intensity data for use in detecting and imaging said regions of interest assembling at least one group of said plurality of parallel frames;

acquiring a two-dimensional specified projection characteristic frame such as a maximal intensity projection (MIP) frame comprised of a plurality of pixels arranged in a two-dimensional array wherein each pixel contains the maximum intensity, any fraction thereof or any derived function of the plurality of pixels along a ray through all similarly placed pixels in the plurality of parallel frames of the group;

determining the third dimension of each pixel that contains the maximum intensity along the ray;

storing the determined third dimensions;

placing the cursor on a region of interest, as indicated by a hot spot in the MIP;

fetching the three-dimensional location and intensity data responsive to the position of the cursor; and generating axial, coronal and sagittal images, using the fetched data.

In yet another aspect of the present invention the plurality of parallel frames are coronal frames.

In accordance with yet another aspect of the present invention, the plurality of parallel frames are sagittal frames.

In another aspect of the present invention the plurality of parallel frames are axial frames.

In accordance with yet another aspect of the present invention, the parallel frames can be in non-orthogonal directions i.e., oblique directions.

In yet another preferred aspect of the present invention, the third dimension is stored in a virtual frame that is never displayed, thus the two dimensions of the maximum intensity frame reveals the third dimension to precisely locate the maximum intensity pixels. Thus, when the cursor is clicked on a given location, for example the X,Y location, a "fetch" order is directed to the virtual frame which provides a Z dimension. Thus, the virtual frame primarily provides dimensional data.

According to yet another preferred aspect of the present invention, a method is provided for expeditiously locating and displaying regions of interest in a patient.

BRIEF DESCRIPTION OF THE DRAWINGS

The features of the invention believed to be novel are set forth with particularity in the appended claims. The invention itself, however, regarding organization apparatus and operation together with further objects and advantages thereof may best be understood by reference to the following description taken in conjunction with the accompanying drawings, which:

FIG. 5 is a two-dimensional coronal MIP frame produced in accordance with a preferred embodiment of the invention;

FIG. 6 is a virtual frame that defines a third dimension for each of the pixels of the MIP frames in accordance with a preferred embodiment of the invention; and FIGS. 7A–C show axial, coronal, and sagittal planes acquired by clicking on the coronal MIP frame of FIG. 5, in accordance with a preferred embodiment of the invention.

DETAILED DESCRIPTION OF THE INVENTION

Figures 1, 2:
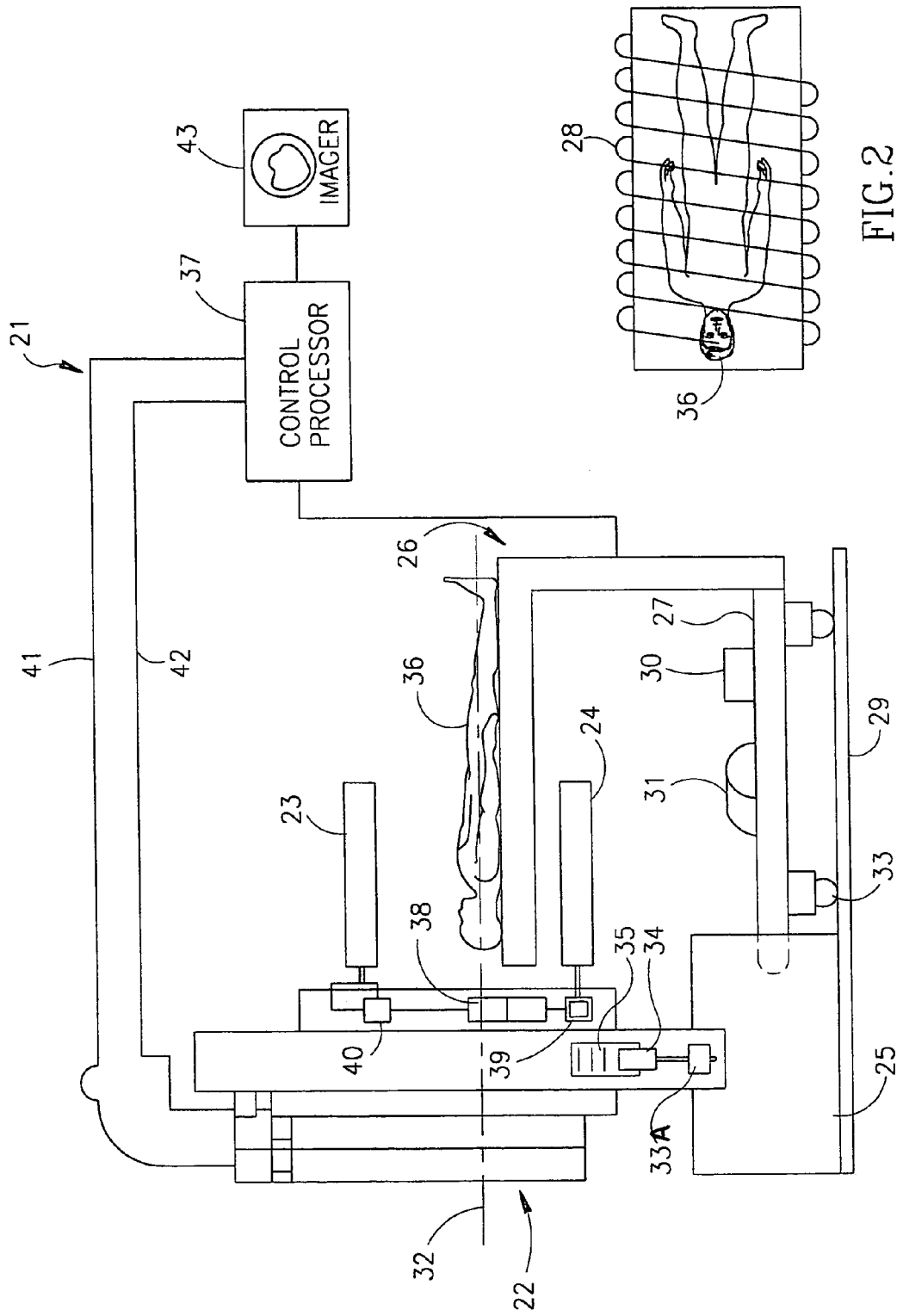
FIG. 1 is a schematic block diagram showing a preferred ECT system for carrying out the invention.
FIG. 2 shows a schematic illustration of a helical whole-body scan.

A SPECT system, also sometimes referred to as an emission computerized tomographic (ECT) system 21 of FIG. 1 includes a gantry 22 on which are mounted detectors, such as first detector head 23 and an oppositely-disposed second detector head 24. Within the scope of the invention a single detector head or more than two detector heads can be used. Equipment such as this is well-known in gamma camera nuclear medicine imaging field. It is described in detail in U.S. Pat. No. 5,554,848, the disclosure of which is hereby included herein by reference. Detector heads 23 and 24 are mounted, spaced apart from each other, with room therebetween for the insertion for a patient table 26, which may be mounted on its own mobile base 27. Gantry 22 is shown as including a non-rotating stationary gantry base 25. In the ECT system of FIG. 1, the gantry rotates the detector heads about a central axis 32. The rotation may be accomplished by any well-known means, such as a motor 33A operated in conjunction with gears 34 and 35. The rotating gantry causes detector heads 23 and 24 to rotate about a patient shown at 36. Detector heads 23 and 24 are capable of moving towards and away from the patient through the use of such apparatus as a motor 38 cooperating with gear arrangements 39 and 40. Motor 38, along with gears arrangements 39 and 40 are used to maintain the detector heads proximate to the patient at all times. Thus, the detector heads are maintained juxtaposed to the patient in a non-circular orbit.

To provide a helical scan about patient 36 as demonstrated in FIG. 2, means are provided for moving table 26 and scanners 32 relative to each other. Thus, one arrangement providing relative motion is shown in FIG. 1 as a motor 31, operating in conjunction with a gear box 30 to move table 26 relative to gantry 22. The motor and gear arrangement rotates wheels such as a wheel 33, moving table 26 along a rail 29.

Within the scope of the invention, the scan does not have to be helical. It can be a plurality of separate orbital scans made while there is no relative longitudinal motion between the patient and the scanner; in which case the bed is moved relative to the scanner in steps prior to each rotation of the scanner about the patient. Furthermore, while the scanner shown in FIG. 1 is of the SPECT type, the invention is equally applicable to other 3-D imaging systems such as STET, PET, etc.

Detector heads 23 and 24 detect emitted gamma rays, for example. The gamma rays strike the detectors, which include scintillators which scintillate in response to the impact of the gamma rays. Photo-multiplier tubes are included in the detectors, and convert the light flashes of the scintillators into electrical signals, in the well-known manner of gamma radiation nuclear medicine imaging. The electrical signals are sometimes referred to as beta signals. The beta signals are transmitted by conductors such as conductors 41, 42 to a control processor 37. The control processor converts the beta signals into images in a well-known manner. The image thus provided is displayed on the image or display monitor 43.

Figure 3:
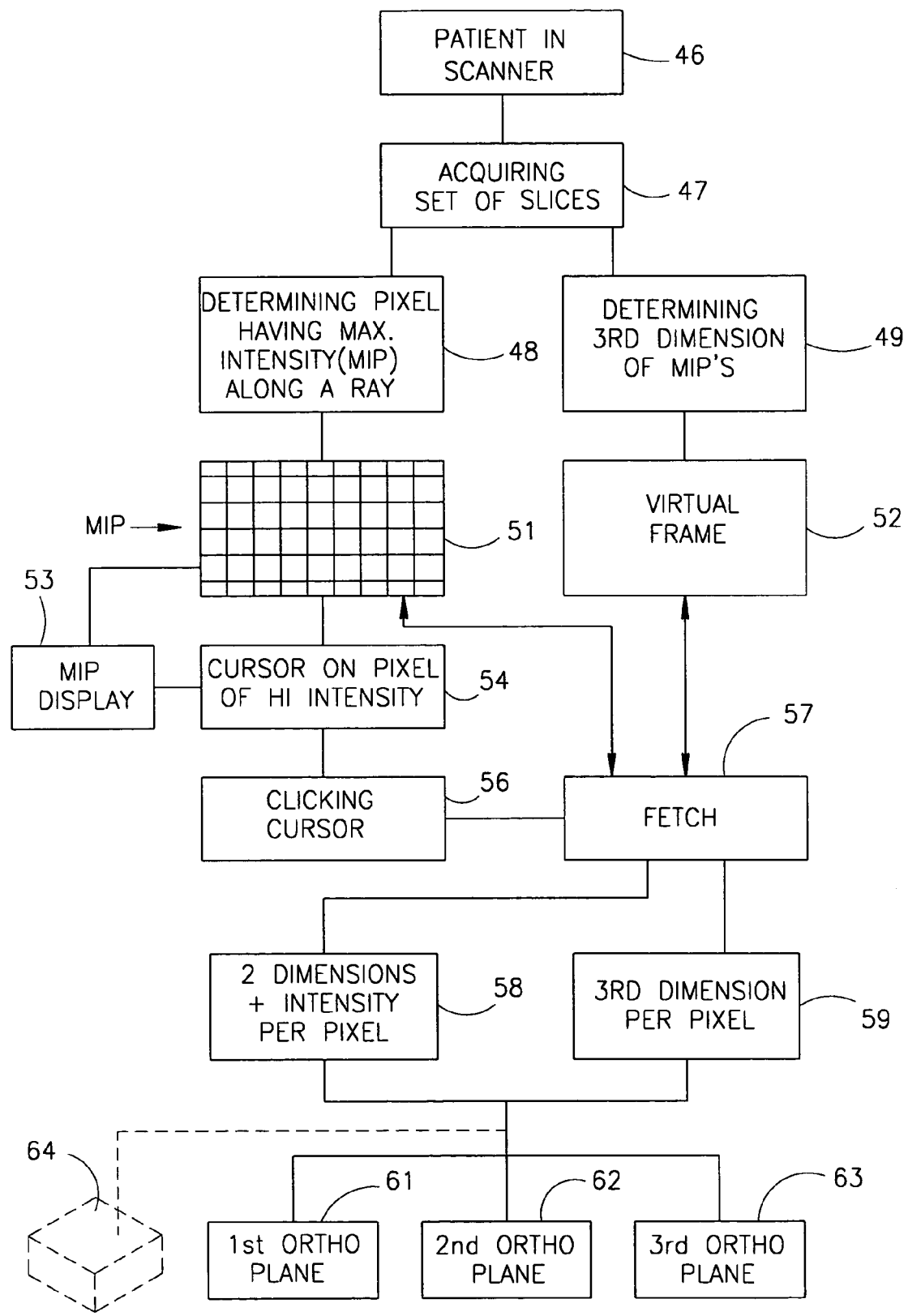
FIG. 3 is a flow chart showing a method according to a preferred embodiment of the invention.

The flow diagram of FIG. 3 outlines a method for determining the 3-D position of a lesion (hot spot) in accordance with a preferred embodiment of the invention. The method, in block 46, calls for positioning the patient or object in a scanner such as scanner 21. The scanner is then operated to acquire a set or group of images of slices, as indicated in block 47.

From a stacking of the group of slices, the maximum intensity pixel is determined in straight line rays or projections perpendicular to the stack of slices and going through all of the pixels similarly placed in each slice. The maximum intensity pixel two-dimensional location and intensity for each ray is determined and posted in an MIP frame. The determination of the MIP frame is shown in block 48.

While finding the maximum intensity pixel along each ray, a determination is also made of the third dimension location of each of the maximum intensity pixels for each pixel in the MIP frame. The determination of the third dimension of each of those pixels is shown in block 49.

From the determination of the maximum intensity pixels, a two-dimensional maximum intensity projection (MIP) frame 51 is assembled, based on the first and second dimensions, and locations of each of the maximum intensity pixels in the MIP frame. This frame can be considered as a projection image of the stack, with the highest value in the projection shown. At the same time, the third dimension of each of the pixels that have the maximum intensity along each ray is stored in a virtual frame 52. Thus, for example, if frame 51 is defined by X and Y coordinates, then for each of the X and Y coordinates frame 52 would provide a Z value, or a depth measurement of the position in the Z direction of the highest value pixel.

The MIP frame assures that it is relatively easy to determine a lesion, since a lesion is hot, and therefore brighter than surrounding pixels; i.e., the pixels of the lesion are brighter than surrounding pixels. The MIP frame is displayed on the monitor as indicated in block 53. The position of the lesion on the MIP frame is determined either automatically or by the operator. For example, in accordance with a preferred embodiment of the invention a cursor is placed somewhere on the lesion, as indicated by block 54. The cursor on the lesion is clicked, as shown in block 56. This, according to a preferred embodiment of the invention, initiates a fetch command. The fetch command indicated by block 57 assembles both the two-dimensional locational values, as shown in block 58 and the third dimension of the virtual frame shown in block 59, plus optionally the intensity of the pixel that the cursor is on.

With this information, three orthogonal planes can be displayed, as shown at blocks 61 for example for the sagittal frame, 62 for the coronal frame and 63 for the axial frame. Preferably each of these images contain the lesion. This enables an automatic display of the lesion in the three orthogonal planes, or a three-dimensional image shown in dashed lines at 64 can be easily developed with the information at hand. Alternatively, any one or two orthogonal slices containing the lesion are shown. Alternatively or additionally, several slices around the lesion are shown (for example in a cine mode or side-by-side) to provide a view of the entire lesion and its surroundings.

Figure 4A:
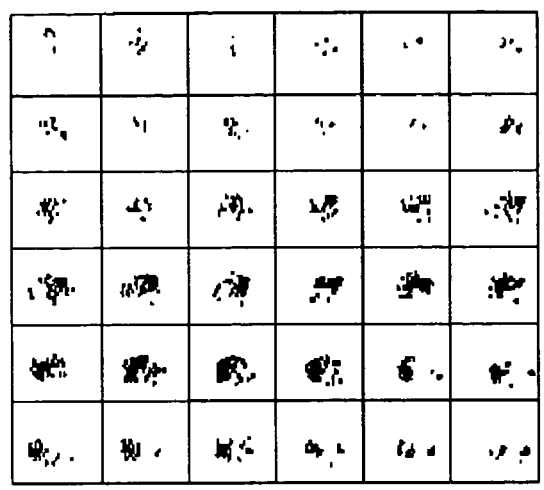
FIG. 4A is a collection of images of slices in the axial direction.
Figure 4B:
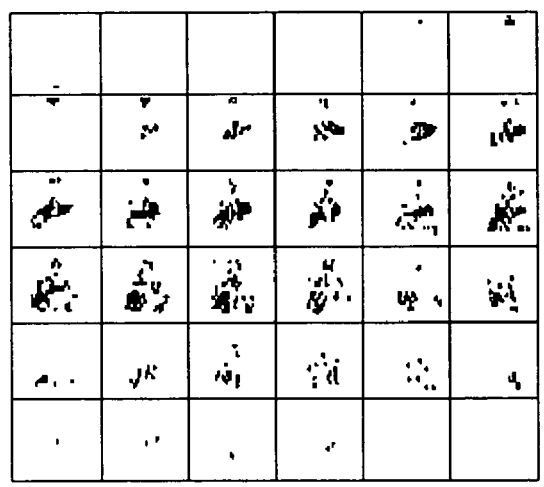
FIG. 4B is a collection of images of slices in the coronal direction.
Figure 4C:
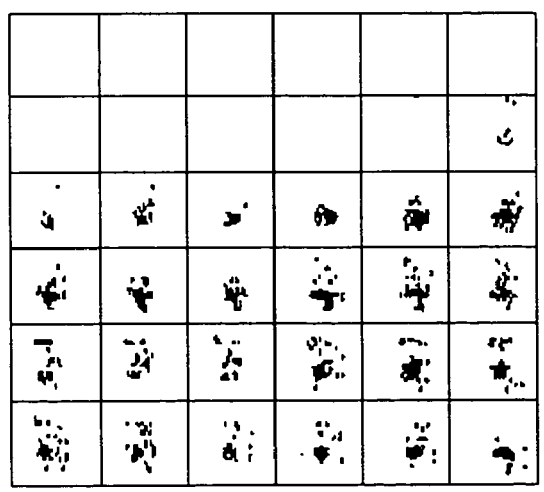
FIG. 4C is a collection of images of slices in the sagittal direction.

FIG. 4A shows a group of axial slices, while FIG. 4B shows a group of coronal slices, and FIG. 4C shows a group of sagittal slices. In each figure the slices are arranged side by side as they would be on a standard display or hard copy. Bright spots indicated in the slices are caused by the lesions.

The lesion is more clearly depicted in FIG. 5, a coronal MIP. It would also be shown in the sagittal MIP, or an axial MIP.

If a cursor is placed on the lesion, as indicated by the origin of arrow 66 in FIG. 5, the coronal MIP, and the cursor is clicked, then the computer provides fetch commands to fetch the data necessary for providing orthogonal images.

FIG. 6 shows a frame used for storage of depth information for each of the maximum-intensity pixels depicted in the MIP. Thus, for example, if the virtual frame of FIG. 6 is an X-Z frame, then Y values will be stored at the X-Z locations, so that when an X-Z location from an MIP is known, the depth value Y is immediately called out in the virtual frame of FIG. 6.

The virtual frame does not need to be displayed. While a frame type memory is shown, other type memories can be used within the scope of the invention. Finally, FIG. 7A shows the three orthogonal images 7A, 7B and 7C, automatically provided for example by clicking on the lesion. Three orthogonal views at the origin of arrow 66 provides a 3-D location, as emphasized with the hot circle in each of the axial (FIG. 7A), coronal (FIG. 7B) and sagittal (FIG. 7C) images. More particularly, the circles are shown at 67, 68 and 69, in FIGS. 7A, 7B and 7C. Thus, by determining the third dimension at the same time as determining the first and second dimension of the pixel having the maximum intensity, it becomes possible to simultaneously create MIP and third dimension frames. The addition of a user interface, as shown in FIG. 1, which senses a mouse click and responds to the mouse click with a "fetch" command enables the display of the region of interest; i.e., the lesion indicated by a selected pixel of the MIP frame Thus, the necessity of reviewing up to 200 images of the group of images is eliminated.

It should be apparent that the embodiment described herein is merely exemplary, and that a person skilled in the art may make many variations and modifications to the embodiments as described herein. Any and all such variations or modifications, as well as others, which may become apparent to those skilled in the art, are intended to be included within the scope of the invention as defined by the appended claims.

The terms "include", "comprise" and "have" and their conjugates, as used herein mean "including but not necessarily limited to."

What is claimed is:

1. A method of locating a region of interest (ROI) within a patient from a plurality of parallel frames of two-dimensional intensity data, comprising:
    assembling at least one group of said plurality of parallel frames;
    generating a two-dimensional projected frame of pixels of a specified characteristic intensity projection for the parallel frames of the group;
    determining third dimensional data for each pixel in the projected frame, said third dimension comprising the depth of a frame having the specified characteristic for each pixel in the projected frame; and
    locating the ROI by selecting a pixel in the two-dimensional projected frame
    wherein the specified characteristic is the maximal projected intensity, and the two-dimensional projected frame is a maximal intensity projected (MIP) frame or wherein the specified characteristic is a function of the maximal intensity projection.

2. The method of locating a region of interest (ROI) within a patient from a plurality of parallel frames of two-dimensional intensity data of claim 1 wherein the specified characteristic is the maximal projected intensity, and the two-dimensional projected frame is a maximal intensity projected (MIP) frame.

3. The method of claim 2 wherein selecting the pixel in the two-dimensional frame comprises selecting a pixel having the highest intensity.

4. The method of claim 2 wherein selecting the pixel in the MIP frame comprises selecting a pixel from among a group of pixels with higher than average intensities.

5. The method of claim 2 and including storing of the third dimensional data, wherein the storing of the third dimensional data comprises storing the data in a virtual frame.

6. The method of claim 1 wherein the specified characteristic is a function of the maximal intensity projected (MIP).

7. The method of claim 1 wherein selecting the pixel in the two-dimensional frame comprises selecting a pixel that contains a function of the specified characteristic.

8. The method of claim 1 comprising determining the intensities of pixels with higher than average intensities in the region of the selected pixel; and
    displaying the ROI using the determined third dimensional data and intensities of the pixels in the region of the selected pixel.

9. The method of claim 1 wherein selecting is performed manually.

10. The method of claim 1 including:
    causing the patient to ingest a radionuclide; and
    acquiring the plurality of parallel frames using a gantry including gamma radiation detectors for detecting the gamma radiation emitted by the patient after ingesting the radionuclide.

11. The method of claim 10 wherein the gantry causes gamma radiation detectors to perform a helical scan of the patient.

12. The method of claim 10 wherein the gantry causes the gamma ray detectors to perform a plurality of orbital scans.

13. The method of claim 10 wherein the gantry causes the detectors to perform an orbital scan that is non-circular, maintaining the detectors in close proximity to the patient during the orbital scan.

14. The method of claim 1 wherein the parallel frames are coronal views.

15. The method of claim 1 wherein the parallel frames are sagittal views.

16. The method of claim 1 wherein the parallel frames are axial views.

17. The method of claim 1 wherein the parallel frames are oblique views.

18. A method of locating a region of interest (ROI) within a patient from a plurality of parallel frames of two-dimensional intensity data, comprising:
    assembling at least one group of said plurality of parallel frames;

generating a two dimensional projected frame of pixels of a specified characteristic intensity projection for the parallel frames of the group;

determining third dimensional data for each pixel in the group, said third dimension comprising the depth of a frame having the specified characteristic for each pixel in the projected frame; and locating the ROI by selecting a pixel in the two-dimensional projected frame, wherein the specified characteristic is the maximal projected intensity, and the two-dimensional projected frame is a maximal intensity projected (MIP) frame, and including:

storing the third dimensional data;

locating a cursor on the selected pixel in the MIP suspected of indicating an ROI;

clicking on the cursor located on the pixel in the MIP;

fetching the two-dimensional data of the two dimensions and intensity from pixels in the vicinity of the cursor located in the MIP and the stored third dimensional data responsive to the click on the cursor; and generating images using the fetched data.

19. The method of claim 18 wherein said images generated using fetched data are orthogonal images.

20. The method of claim 18 wherein the images generated using the fetched data are 3-dimensional images.

21. The method of locating and imaging a region of interest within a patient of claim 18 wherein the region of interest is a lesion and wherein the cursor is located on a hot spot in the MIP suspected of indicating a lesion.

22. A method of locating a region of interest (ROI) within a patient from a plurality of parallel frames of two-dimensional intensity data, comprising:

assembling at least one group of said plurality of parallel frames;

generating a two-dimensional projected frame of pixels of a specified characteristic intensity projection for the parallel frames of the group;

determining third dimensional data for each pixel in the group, said third dimension comprising the depth of a frame having the specified characteristic for each pixel in the projected frame; and locating the ROI by selecting a pixel in the two-dimensional projected frame, wherein the specified characteristic is the maximal projected intensity, and the two-dimensional projected frame is a maximal intensity projected (MIP) frame, and including:

storing of the third dimensional data, wherein the storing of the third dimensional data comprises storing the data in a virtual frame; and storing third dimensional data in the virtual frame at the two dimensions that locate the maximum intensity pixel of each of the pixels of the MIP frame.

* * * * *